US011375937B2

(12) United States Patent
Souhoka et al.

(10) Patent No.: US 11,375,937 B2
(45) Date of Patent: Jul. 5, 2022

(54) ELECTRODE CARRIER FOR ELECTROPHYSIOLOGICAL MEASUREMENT

(71) Applicant: PROLIRA B.V., Utrecht (NL)

(72) Inventors: Tessa Souhoka, Utrecht (NL); Marlies Van Dullemen, Utrecht (NL)

(73) Assignee: PROLIRA B.V., Utrecht (NL)

( * ) Notice: Subject to any disclaimer, the term of this patent is extended or adjusted under 35 U.S.C. 154(b) by 517 days.

(21) Appl. No.: 16/472,312

(22) PCT Filed: Dec. 21, 2017

(86) PCT No.: PCT/EP2017/084215
§ 371 (c)(1),
(2) Date: Jun. 21, 2019

(87) PCT Pub. No.: WO2018/115349
PCT Pub. Date: Jun. 28, 2018

(65) Prior Publication Data
US 2020/0383594 A1     Dec. 10, 2020

(30) Foreign Application Priority Data
Dec. 21, 2016   (NL) ..................... 2018031

(51) Int. Cl.
*A61B 5/05*     (2021.01)
*A61B 5/273*    (2021.01)
(Continued)

(52) U.S. Cl.
CPC ............... *A61B 5/273* (2021.01); *A61B 5/24* (2021.01); *A61B 5/6832* (2013.01);
(Continued)

(58) Field of Classification Search
CPC .......... A61B 5/282; A61B 5/25; A61B 5/0006; A61B 5/316; A61B 5/349; A61B 5/259;
(Continued)

(56) References Cited

U.S. PATENT DOCUMENTS

| 6,434,410 B1 * | 8/2002 | Cordero | ................. A61B 5/282 600/396 |
| 7,206,630 B1 | 4/2007 | Tarler | |

(Continued)

FOREIGN PATENT DOCUMENTS

| EP | 1854403 A2 | 11/2007 |
| JP | H02-051505 U | 4/1990 |

(Continued)

OTHER PUBLICATIONS

Japanese Office Action dated Oct. 20, 2021 for family member Application No. 2019-534873.

*Primary Examiner* — Joseph A Stoklosa
*Assistant Examiner* — Brian M Antiskay
(74) *Attorney, Agent, or Firm* — Hudak, Shunk & Farine Co. LPA

(57) ABSTRACT

Electrode carrier for electrophysiological measurements, including a flexible substrate, a plurality of contact pads attached to a substrate surface, wherein each contact pad includes conductive means for accommodating an electrode for electrophysiological measurement, first connecting means attached to the substrate for communicatively connecting the contact pads to a signal processing device. The first connecting means includes a plurality of conductive tracks on the substrate surface for electrically connecting the plurality of contact pads, wherein each conductive track corresponds to at least one contact pad. The substrate has at least two inextendible sections for accommodating the contact pads, wherein the sections interconnected by an extendible section. Each extendible section comprises at least one (Continued)

warpable member of flexible material. At least one of the warpable members accommodates at least one of the conductive tracks. The at least one warpable member includes a V-shaped portion of the substrate, and the extendible section includes four warpable members are arranged in an X-shaped fashion.

20 Claims, 5 Drawing Sheets

(51) Int. Cl.
*A61B 5/00* (2006.01)
*H05K 1/02* (2006.01)
*A61B 5/24* (2021.01)
*A61B 5/259* (2021.01)
*A61B 5/282* (2021.01)
*A61B 5/291* (2021.01)
*A61B 5/296* (2021.01)

(52) U.S. Cl.
CPC ......... *H05K 1/0216* (2013.01); *H05K 1/0296* (2013.01); *A61B 5/259* (2021.01); *A61B 5/282* (2021.01); *A61B 5/291* (2021.01); *A61B 5/296* (2021.01); *A61B 2562/0215* (2017.08); *A61B 2562/0217* (2017.08); *A61B 2562/125* (2013.01); *A61B 2562/164* (2013.01); *A61B 2562/166* (2013.01); *A61B 2562/182* (2013.01); *H05K 1/028* (2013.01); *H05K 2201/0715* (2013.01)

(58) Field of Classification Search
CPC . A61B 5/0205; A61B 5/0245; A61B 5/02438; A61B 5/332; A61B 5/6831; A61B 5/287; A61B 5/6833; A61B 5/24; A61B 2560/0412; A61B 5/7203; A61B 5/6804
USPC ............... 600/372, 382–393, 508–509
See application file for complete search history.

(56) References Cited

U.S. PATENT DOCUMENTS

| | | | |
|---|---|---|---|
| 2002/0099277 A1* | 7/2002 | Harry .................. | A61B 5/0002 600/301 |
| 2004/0073127 A1* | 4/2004 | Istvan .................. | A61B 5/259 600/513 |
| 2008/0287770 A1* | 11/2008 | Kurzweil ............. | A61B 5/08 600/388 |
| 2011/0077497 A1* | 3/2011 | Oster ................... | A61B 5/274 600/372 |
| 2012/0246795 A1* | 10/2012 | Scheffler ............ | A41D 13/0007 2/69 |
| 2013/0345539 A1* | 12/2013 | Quintanar ............ | A61B 5/291 600/385 |
| 2014/0378848 A1* | 12/2014 | Tambe ................. | A61B 5/02438 600/483 |
| 2016/0262649 A1* | 9/2016 | Hayes-Gill .......... | A61B 5/6833 |
| 2018/0049698 A1* | 2/2018 | Berg .................... | A61B 5/296 |

FOREIGN PATENT DOCUMENTS

| | | |
|---|---|---|
| JP | 2004512864 A | 4/2004 |
| JP | 2014008166 A | 1/2014 |
| JP | 2016537068 A | 12/2016 |
| WO | 0205700 A2 | 1/2002 |
| WO | 2015056027 A1 | 4/2015 |

* cited by examiner

ELECTRODE CARRIER FOR ELECTROPHYSIOLOGICAL MEASUREMENT

FIELD OF THE INVENTION

The invention relates to an electrode carrier for electrophysiological measurement.

BACKGROUND OF THE INVENTION

Electrode carriers in the art are utilized in combination with suitable electrodes for measurement of electrophysiological signals from a subject's body which signals are used for direct feedback, diagnosis or monitoring. Examples of such electrophysiological signals are signals from the brain for making an electro-encephalogram (EEG), from the heart for making an electrocardiogram (ECG), and from a muscle for making an electromyogram (EMG).

An example of EEG monitoring can be monitoring a subject for the occurrence of a delirium, epilepsy episode or similar deviation. The EEG of the subject allows electronic detection of an episode wherein the ailment may be manifest. Sometimes, monitoring for an extended period of time is required to detect the episode. When detected, adequate action can be taken by responsible practitioners such as for example nurses or physicians in hospital wards, or intensive care unit (ICU) staff.

For making an EEG, electrodes are placed on the subject's skin, i.e. scalp for performing the required measurements of electrical activity of the brain. For detection of an episode with a deviation from a normal EEG or by finding specific EEG patterns however, it is often not required to make a full EEG using, for example, in 21 electrode locations in a—so-called—10/20 measurement setup. In delirium detection, for example, three electrodes may suffice, e.g. two frontal electrodes attached to the forehead and one attached to the back of the head.

Electrodes for this purpose are available in the art which can be individually attached to the subject, requiring an electrical connection to signal processing equipment for each electrode. Also electrode caps or headbands are known having multiple electrodes which are connectable to signal processing equipment. For the electrical connection, a cable or wire can be utilized. Such caps or headbands may be uncomfortable to wear and generally require head size measuring, cap or headband size selection as well as storage and production of several sizes e.g. S-M-L and/or adjusting means such as buckles, or elastic or resilient members i.e. clips, plasters, or clamps to fit the specific subject's head.

Clamping electrode carriers can be bulky having buckles or clips to overcome size differences for different subjects. Such carriers may have loose wiring for connecting the electrode to signal processing equipment, which can be experienced as uncomfortable, time consuming to set up, and hindering the subject.

Electrode carriers for re-use with different subjects require thorough cleaning and sterilization in clinical circumstances.

SUMMARY OF THE INVENTION

It is an object of the invention to provide an electrode carrier for electrophysiological measurements, which overcomes the disadvantageous and problems as set out above.

The object is achieved in an electrode carrier for electrophysiological measurements, comprising a flexible substrate, a plurality of contact pads attached to a substrate surface, wherein each contact pad comprises conductive means for accommodating an electrode for electrophysiological measurements, first connecting means attached to the substrate for communicatively connecting the contact pads to a signal processing device. The first connecting means comprise a plurality of conductive tracks on the substrate surface for electrically connecting the plurality of contact pads, wherein each conductive track corresponds to at least one contact pad. The substrate has at least two inextendible sections for accommodating the contact pads, wherein the at least two inextendible sections are interconnected by an extendible section. Each extendible section comprises at least one warpable member of flexible material. At least one of the warpable members accommodates at least one of the conductive tracks.

In the original state of the extendible portion, the at least one warpable member is flat. The substrate material of the warpable member can be warped by pulling apart the ends of the warpable member. This extending occurs when the inextendible portions of the electrode carrier are pulled apart, causing warping, i.e. elastically twisting, and/or bending of the warpable member. When the inextendible portions of the electrode carrier are released, the warping, or twisting and bending is reversed allowing the at least one warpable member, and thereby the extendible portion, to return to its original flat state.

Thus, the flexible carrier is provided of which a part facilitates an elongation function in one dominant direction, which allows accommodation of the electrode carrier for different body dimensions, i.e. relating to different body parts such as head or limb, torso, or different subjects able to wear a carrier with the same dimensions, thereby facilitating electrophysiological measurements such as EEG, EMG, ECG to be facilitated all over a subject's body. No size adjustment parts such as buckles are required as the extendible part overcomes size differences, one size fits all.

The contact pads and conductive tracks applied to the substrate provide a fixed, integrated electrical connection and are thereby easy to place and obviate loose wiring, which may otherwise discomfort the subject. The electrode carrier provides universal fit on different body parts and more specifically can be applied to small, large, and oddly shaped heads. In case of measuring EEG, it can be worn on both sides of the head for subjects sitting up or lying down. Electrodes can be applied on the contact pads of the inextendible sections. More than one inextendible section can be interconnected to other inextendible sections separated by extendible sections.

In an embodiment, the substrate is formed from a single sheet of flexible material. The electrode carrier being fabricated on a substrate of a single sheet of flexible material allows a layered construction of contact pads, conductive tracks, electrode lining or linings, insulation and adhesive, which makes the electrode carrier particularly suitable for short term use, wherein a subject may wear the carrier for a time after which the electrode carrier may be prepared for another short period of use or be disposed of. The design comprising thin layers also allows for minimal storage space.

In an embodiment, at least one warpable member comprises a V-shaped or loop-shaped portion of the substrate. This allows extension of the ends of the warpable member by warping or resiliently deforming of a portion of the substrate material. Thus, no other separate extendible components are required to be integrated in the carrier to achieve the extendibility of the extendible portion of the electrode carrier.

In an embodiment, the extendible section comprises a plurality of in series interconnected warpable members. By interconnecting the warpable members in series, a larger extension range can be achieved than the extension range for a single member. This can be particularly useful for application of the electrode carrier on large body parts, for example the belly, where more flexibility or extendibility may be required.

In an embodiment, the extendible section comprises a plurality of parallel interconnected warpable members. By interconnecting the warpable members in parallel, a higher modulus of elasticity can be achieved than the elasticity modulus for a single member. This may be particularly useful for application of the electrode carrier on body parts which are exposed to motion when used in exercise, or body parts that for example experience friction against other objects such as clothing or bedding.

In an embodiment, the extendible section comprises four warpable members arranged in an X-shaped fashion. This allows for a compact design and extendibility combined with relative transverse angular stability between the inextendible sections in the longitudinal direction.

In an embodiment, the four warpable members are grouped in two parallel connected strings of two warpable members, wherein a center part of the two series connected warpable members are interconnected using an interconnection member.

This prevents the warpable members from twisting in a longitudinal direction, thereby enhancing transverse angular stability between the inextendible sections.

In an embodiment, at least one of the inextendible sections of the substrate is provided with two contact pads and wherein at least one other inextendible section of the substrate is provided with a single contact pad. This allows the inextendible section having two contact pads to be advantageously placed on a subject's forehead, whereas the inextendible section with a single electrode can be placed in a region opposite of the subject's forehead, for example to the back of the subject's head, or to the crown of the subject's head (Pz location).

In an embodiment, the contact pads are provided with a first connecting means for attaching a removable electrode for electrophysiological measurement. This allows the use of pre-packaged mass-produced electrodes, which can be disposed of after use. The electrode carrier can simply be reused with new electrodes after used electrodes have been removed.

In an embodiment, at least one of the contact pads comprises an electrode lining for electrophysiological measurement. The contact pads form the conductive base for the electrode lining, which combination forms an electrode directly on the electrode carrier substrate, which can be made of one or multiple material layers. By applying the electrode lining during production of the electrode carrier, an electrode carrier can be provided which is ready for immediate use. Alternatively, the electrode lining can be applied shortly prior to use. This allows the electrode carrier to be easily re-used after removal of the electrode lining of a first or preceding use.

Furthermore, the contact pads thus provided with an electrode lining allow preparation of the electrodes independent from use in a clinical setting. Preparation of each individual electrode separately (e.g., filling the electrode manually with conductive gel or wetting the electrode with water), removal of residue from the electrodes from the subject's skin, etc. is no longer required. Time-consuming procedures that do not fit clinical practice are thereby avoided.

The electrode lining can be pre-fabricated, thus providing controlled, operator-independent, and reproducible electrode characteristics.

In an embodiment, at least one contact pad is provided with a dry electrode lining. This can be applied to the contact pad for example by using an adhesive and/or other mechanical means to attach the dry electrode lining to the contact pad.

In an embodiment, at least one contact pad is provided with a wet electrode lining. Such electrode lining can easily be removed for example by rinsing of the electrode lining from the contact pads. Application of a new electrode lining can be easily provided, for example, by applying the lining from a liquid container onto the contact pad surface.

In an embodiment, at least one contact pad comprises conductive gel or a hydrogel lining electrode.

In an embodiment, the conductive gel or hydrogel lining comprises an adhesive material, or comprises a conductive gel or hydrogel that is adhesive and/or has a high tack, thereby making the contact pads with the electrode lining ready to be attached to the subject's skin surface.

In an embodiment, at least one contact pad has a surrounding adhesive layer with an opening to expose the contact pad with or without an electrode lining. This allows attaching of the electrode carrier to the subject's skin, while keeping the contact pad and/or electrode lining free for making a conductive, i.e. electrical connection with the subject.

In an embodiment, the electrode carrier further comprises a conductive adhesive layer covering at least one electrode. This allows attaching the electrode carrier to the subject's skin surface as an alternative to providing adhesive surrounding the contact pad.

In an embodiment, any adhesive layer is covered by a removable cover layer. This allows the electrode carrier to be fully prepared, ready for use, and requiring only the cover layer to be peeled off for use. Moreover, this allows clean storage and transportation and prevention of the electrode carrier to stick to other objects, more specifically packaging, prior to use.

In an embodiment, the conductive tracks comprise a conductive material selected from at least one of a metal, a conductive plastic material, and a metal containing ink. The tracks can be applied to the substrate by screen-printing, other means of printing, or laminating a conductive layer and removing unused parts using a process such as etching.

In an embodiment, the conductive tracks are covered by an insulation layer. The insulation layer prevents interference by undesired contact of the conductive tracks with for example the subject's skin.

In an embodiment, the electrode carrier is covered by an electromagnetic shielding layer. The electromagnetic shielding layer prevents interference by electromagnetic fields pervading the space around the conductive tracks. The electromagnetic shielding layer can be disposed on the insulation layer. Alternatively or additionally, the electromagnetic shielding layer can also be disposed on the substrate at the side opposite the conductive tracks and contact pads. This way the contact pads can be shielded in particular.

In an embodiment, the electromagnetic shielding layer is connected to any of the conductive tracks with a conductive via penetrating the electrode carrier. The electromagnetic shielding layer can be connected this way to, for example, an earth lead via the first connecting means.

In an embodiment, the first connecting means comprise a connector having terminals, the terminal being electrically connected to the conductive tracks. This provides a wired connection of the electrode carrier to further equipment for processing the electrical signals from the contact pads.

In an embodiment, the first connecting means comprise signal processing means connected to the conductive tracks, the signal processing means being arranged for capturing and processing the electrical signals from the contact pads.

This allows the electrical signals from the contact pads to be processed or preprocessed and monitored locally. In addition, visual signaling means such as LEDs, or audible signaling means such as a beeper may be accommodated on the substrate for indicating a state of the electrical signals from the contact pads to the subject and/or responsible staff when a pattern is detected.

In an embodiment, the signal processing means comprise an output connected to the connector. This allows digital transfer of the electrical signals from the contact pads and any data derived from these signals. This prevents long connections to any further signal processing equipment, thereby reducing interference and noise.

In an embodiment, the first connecting means further comprise a wireless data transfer device communicatively connected to the signal processor. The wireless data transfer device arranged for wirelessly transferring the captured electrical signals and/or a status or information derived from the electrical signals of the contact pads to the signal processor. Moreover, this allows the electrode carrier to be utilized at greater distances from for example a monitoring desk in an ICU without discomfort of interference from long wiring.

DETAILED DESCRIPTION OF EMBODIMENTS

Figure 1:
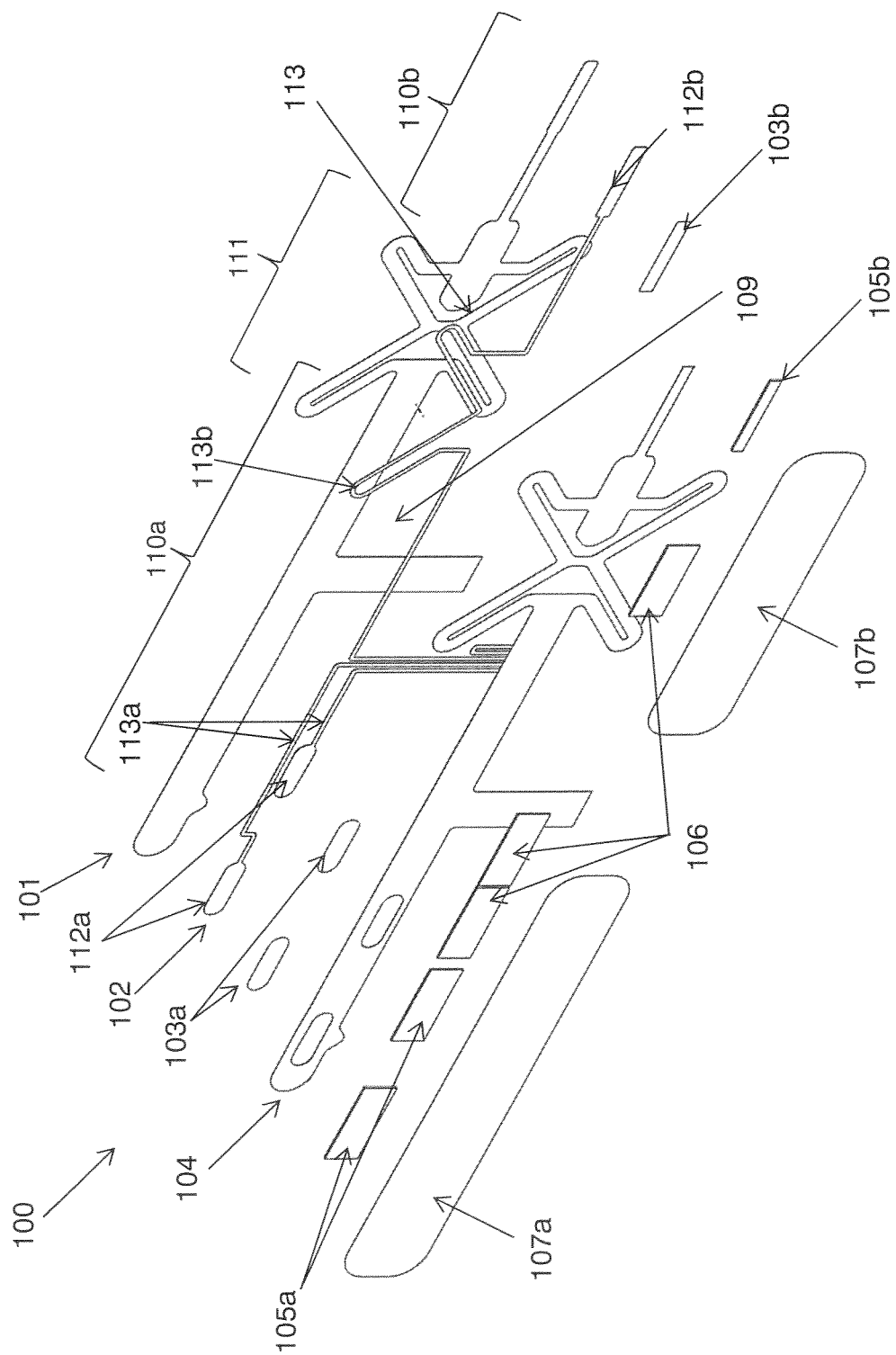
FIG. 1 shows an exploded view of an electrode carrier according to an embodiment of the invention.

In FIG. 1 an electrode carrier 100 is shown, comprising a substrate 101 made of a flexible material. The substrate 101 can for example be manufactured from a flexible plastic or polymer material having insulating properties. The material of the substrate 101 is preferable inextendible. The substrate can be made of a polyester film. Preferably the polyester film is a bi-axial oriented film having minimal elasticity in the longitudinal direction of the electrode carrier 100. The substrate 101 preferably has resilient properties to allow for bending and warping. The substrate 101 has inextendible sections 110a, 110b connected with an extendible section 111. The extendible section 111 is shown in FIG. 1 having members 113 connected in parallel and in series in an X-shape.

On the substrate 101, a conducting layer 102 can be provided having contact pads 112a, 112b mutually disposed on the inextendible sections 110a, 110b of the substrate 101 opposite of the extendible section 111. The conducting layer 102 can be made from metal, such as copper r silver, r conducting ink or conductive polymer. Preferably the conductive layer is made from a conductive coating containing silver. The contact pads 112a, 112b are electronically connectable via conductive tracks 113a, 113b, 113c to a connector which can be provided on a connection section 109 of the substrate. The conductive tracks 113a, 113b, 113c extend from the contact pads 112a to the connection section 109 of the substrate 101. The conductive track 113b corresponding to contact pad 112b passes a warpable member of the extendible section 111 to the connection section 109. A connector for electrically connecting the electrode carrier 100 to processing equipment (not shown in FIG. 1) may be provided on the connection section 109 of the substrate. Moreover, the conductive tracks 113a, 113b, 113c can also be connected to a signal processor disposed anywhere on the substrate 101, for example on connection section 109.

The connection section can extend from for example the inextendible section having two contact pads, however it may be provided at for example one end of the short inextendible section facing the X-shaped extendible section.

The contact pads 112a, 112b, can be provided with an electrode lining 103a, 103b, which is designed to have a shape corresponding to the shape of the contact pads 112a, 112b respectively. The electrode lining 103a, 103b can comprise one or more layers to establish contact between the subject's skin and the contact pads. The electrode lining 103a, 103b can comprise a conductive coating, such as silver-silver chloride (Ag/AgCl) coating, which can be provided as a screen-printed layer which may be matched with a component such as carbon to form a dry electrode. The electrode lining 103a, 103b can also be formed by an AgCl solution or any other suitable electrolyte in an absorber which can be applied to the contact pads 112a, 112b to form wet electrodes. Alternatively, the electrode lining 103a, 103b can be formed by a conductive hydrogel, also to form a wet electrode. The hydrogel lining can be provided with an adhesive component, thereby allowing the contact pad and lining, thus forming the electrode, to be attached to the subject's skin.

On top of the conductive tracks 113a, 113b, 113c, and exposed parts of the substrate 101, an insulating layer 104 can be applied having openings for exposing the contact pads 112a, 112b. On top of the contact pads 112a and/or the electrode linings 103a, 103b, conductive adhesive patches 105a can be applied. The adhesive patches 105a, 105b allow the electrode carrier 100 to be fixed to a subject's skin. Additional adhesive patches 106 can be provided for enhancing and strengthening the fixation of the electrode carrier 100 to the subject skin. The adhesive patches 105a, 105b, 106 can be covered by a peel-off cover layer 107a, 107b. These peel-off cover layers 107a, 107b can be removed shortly before use on a subject.

An electromagnetic shielding layer, not shown in FIG. 1, can be arranged on top of the insulating layer covering the conductive tracks. Alternatively, the electromagnetic shielding layer can be arranged on the substrate at the side opposite of the contact pads. the electromagnetic shielding layer can be made from a conductive material such as a metal or from a conductive polymer. The electromagnetic shielding layer can be connected to one of the conductive tracks 113a, 113b, 113c which can be connected to electrical earth. The connection can be made using one or more vias penetrating through the insulating layer or the substrate.

The signal processor can be provided with one or more amplifiers for amplifying the signals from the contact pads, and an analog to digital converter to capture and digitize the signals from the contact pads. The signal processor can be provided with a memory and program instructions for processing the digitized signal from the contact pads. The processing may comprise filtering such as applying a bandwidth filter, and analyzing the signals for the detection of patterns required for the measurement or monitoring. The signal processor can be a microprocessor or microcontroller, or a dedicated high performance signal processor.

The signal processor and supporting circuitry can be integrated in or on the electrode carrier on at least one of the inextendible parts of the carrier.

The processor can output its processed signal to the connector described above, thus allowing a digital connection to further signal and data processing. The signal; processor in the wired set up, may be supplied from the connector, which is in turn connected to the further signal and data processing equipment. The electrode carrier may be also provided with a battery integrated or attached to the substrate.

Alternatively, the processor can output its processed signal to a wireless communication device which can be arranged for wirelessly communicating the captured and/or processed signals from the contact pads using for example Bluetooth or wireless LAN or near field communication technology.

Figure 2A:
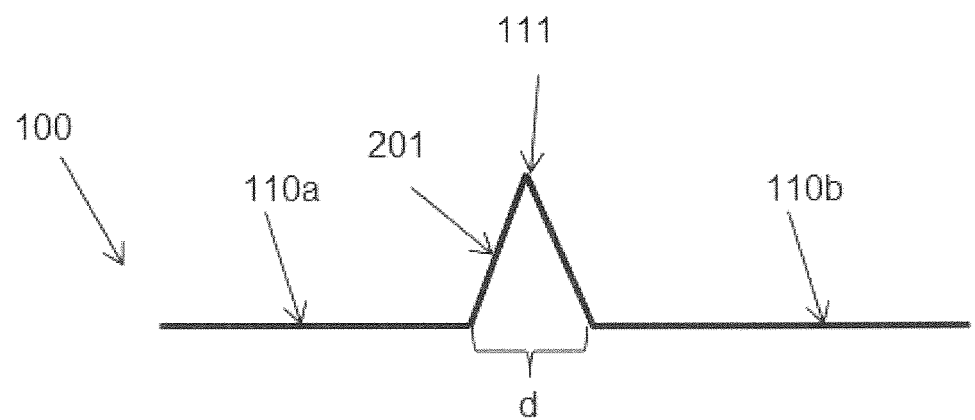
FIGS. 2a-2e show schematic representations of an electrode carrier according to an embodiment of the invention.

In FIG. 2a a schematic view of an electrode carrier 100 is shown having an inextendible section 110a connected via an extendible section 111 to another inextendible section 110b. The extendible section 111 comprises one or more V-shaped member portions 201 of the substrate. The substrate is made of a resilient, flexible material, thus the V-shaped portion 201 is thereby warpable, by twisting or bending. This allows the inextendible sections 110a, 110b to have a variable mutual distance d. The electrode carrier 100 in the example of FIG. 2a has a single member 201.

Figure 2B:
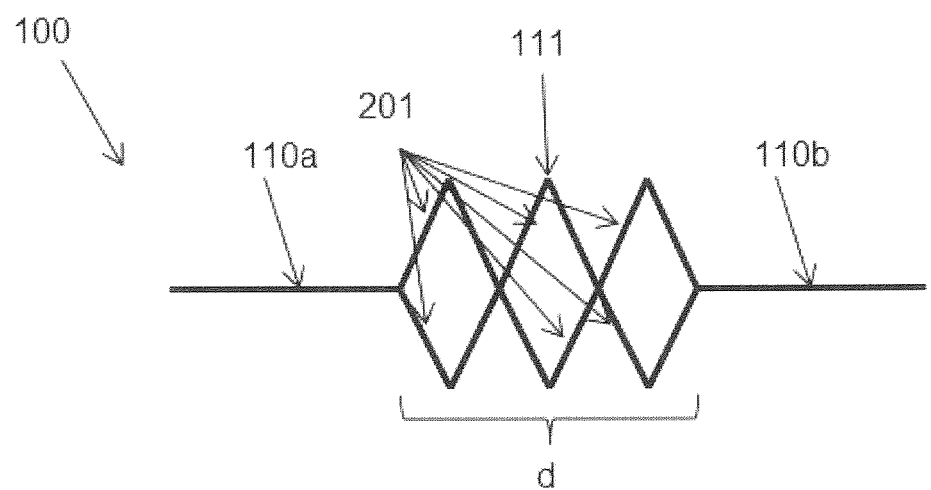

Multiple warpable members 201 can form an extendible section 111. The warpable members 201 can be connected between the inextendible sections 110a, 110b in series and/or in parallel. The extendible section 111 of the example of FIG. 2b has six warpable members 201, pairwise connected in parallel, and the pairs of parallel connected members connected in series to the inextendible sections 110a, 110b. The warpable members 201 in FIG. 2b are shown mutually interconnected, forming cross connections between the members.

Figure 2C:
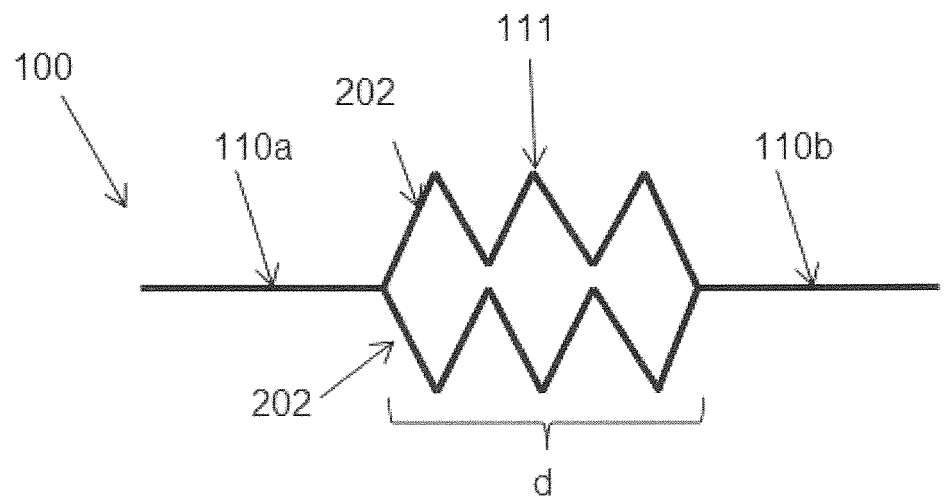

In FIG. 2c an electrode carrier is shown having two strings 202 of warpable members 201 in series, wherein the respective strings 202 are mutually connected in parallel between the inextendible sections 110a, 110b.

Figure 2D:
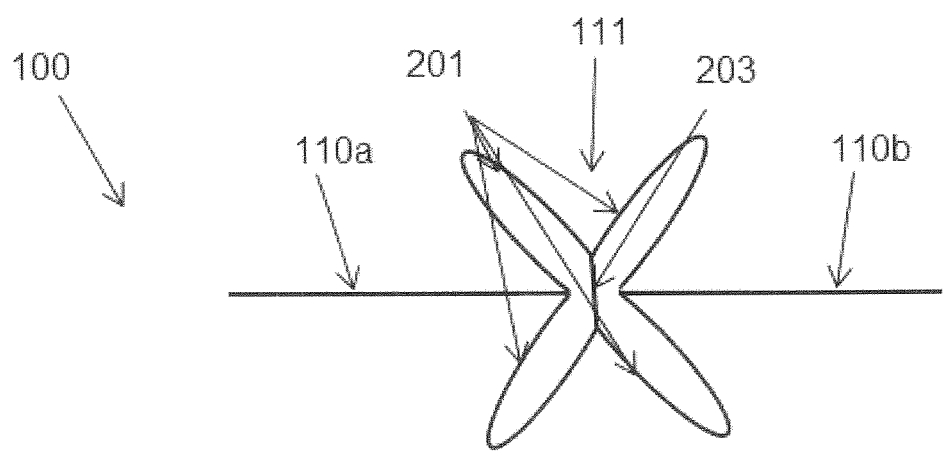

In FIG. 2d the variant of the extendible section 111 of FIG. 1 is shown having four warpable members 201 connected in series and in parallel, wherein each warpable member 201 has a loop shape, which loops are connected on one side to the inextendible sections 110a, or 110b respectively and wherein the opposite end of the loops are interconnected by crossbar 203 as an interconnection member. The loop shaped warpable members 201 provide a longer stretch margin than the straight V-shaped members 201 of FIGS. 2a-2c. The cross bar 203 enhances transverse angular stability between the inextendible sections 110a, 110b.

Figure 2E:
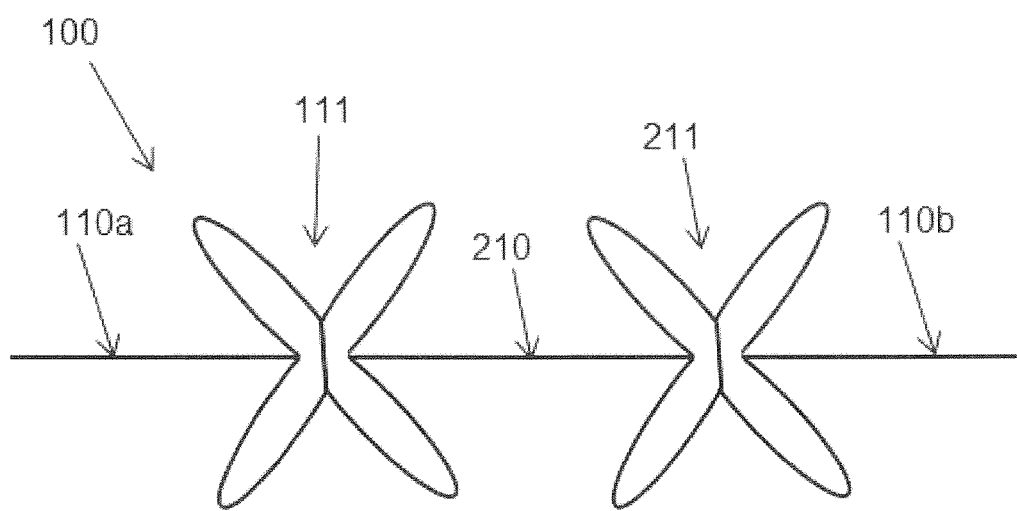

In FIG. 2e a variant of the electrode carrier of FIG. 2d is shown having two extendible sections 111, 211 interconnected by an inextendible section 210. The number of inextendible and extendible sections can vary depending on specific requirements regarding placement of electrodes and stretch.

Figure 3:
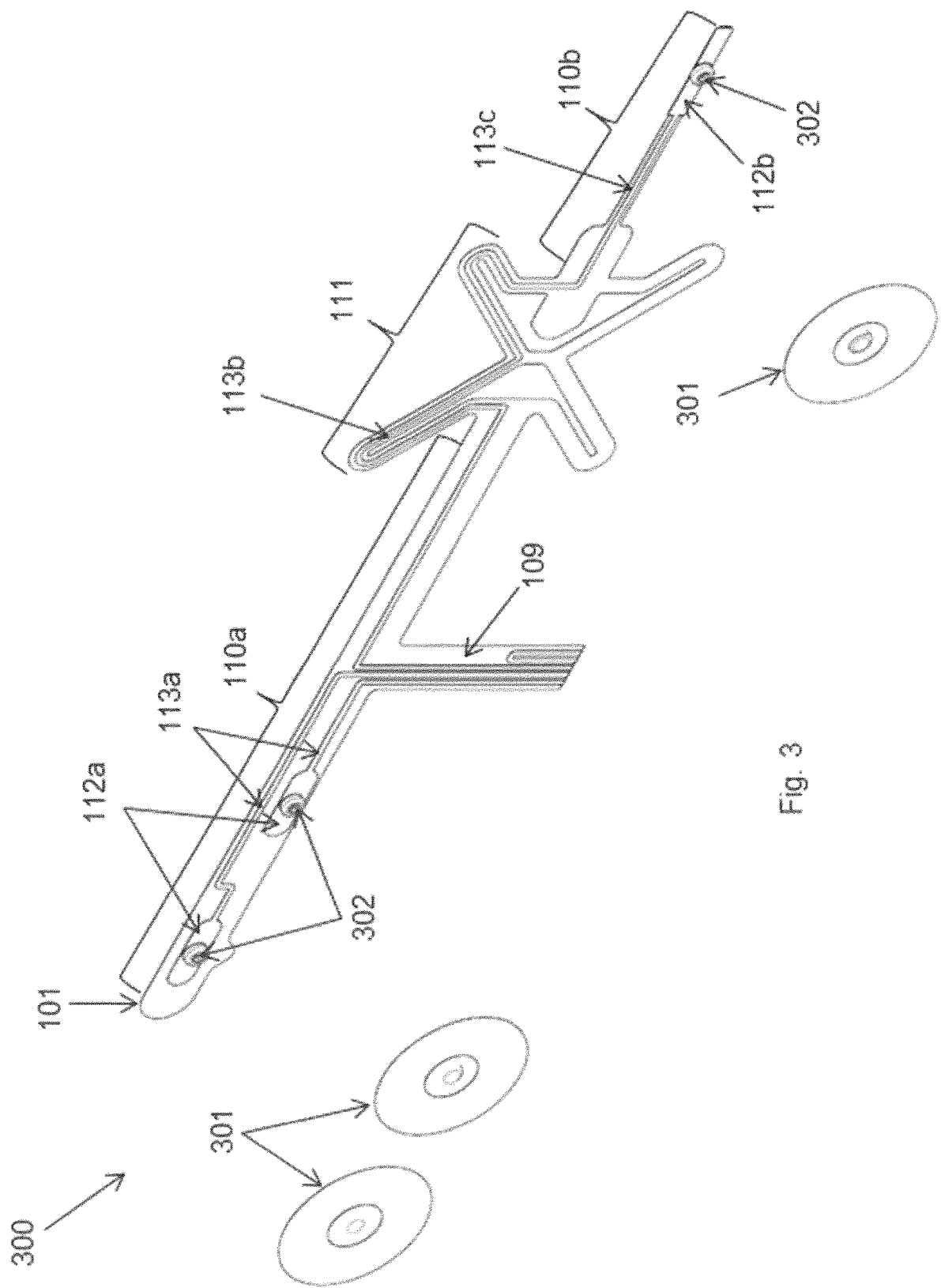
FIG. 3 shows an exploded view of an electrode carrier according to another embodiment of the invention.

In FIG. 3 an electrode carrier 300 is shown having inextendible sections 110a, 110b and an extendible section 111. As shown in FIG. 3, an alternative to the electrode lining 103a, 103b of, the contact pads 112a, 112b can be provided with a conductive connection to which replaceable electrodes can be pressed in a mechanical snap-fit and electrical connection. The contact pads 112a, in FIG. 3 conduct the electrical signals from the replaceable electrodes via the conductive tracks 113a to the connection section 109 of the substrate 101.

In FIG. 3, connection buttons 302 are provided on the contact pads 112a. The buttons 302 are provided with a conductive material and are attached to the contact pads 112a for example by a conductive adhesive or by stapling. The connection buttons 302 have an opening for receiving replaceable electrodes 301. The replaceable electrodes 301 can be provided with conductive protrusions which correspond with the openings in the connection buttons 302 for mechanically and electrically connecting the electrodes.

Alternatively, the contact pads 112a, 112b can be provided with a conductive lug or protrusion on which a replaceable electrode 301 having a corresponding conductive button 302 can be pressed for making the mechanical and electrical connection. Various alternative solutions will be available for the skilled person to connect a replaceable electrode 301 to the electrode carrier 300 as shown in FIG. 3.

In FIG. 3 the inextendible section 110b is shown having a contact pad 112b without button, and connected to the connection section via conductive tracks 113c and 113b, thereby prepared for receiving a wet or dry, or (hydro)gel electrode lining as set out above.

It will be clear to a person skilled in the art that the scope of the present invention is not limited to the examples discussed in the foregoing but that several amendments and modifications thereof are possible without deviating from the scope of the present invention as defined by the attached claims. In particular, combinations of specific features of various aspects of the invention may be made. An aspect of the invention may be further advantageously enhanced by adding a feature that was described in relation to another aspect of the invention. While the present invention has been illustrated and described in detail in the figures and the description, such illustration and description are to be considered illustrative or exemplary only, and not restrictive.

The present invention is not limited to the disclosed embodiments. Variations to the disclosed embodiments can be understood and effected by a person skilled in the art in practicing the claimed invention, from a study of the figures, the description and the attached claims. In the claims, the word "comprising" does not exclude other steps or elements, and the indefinite article "a" or "an" does not exclude a plurality. The mere fact that certain measures are recited in mutually different dependent claims does not indicate that a combination of these measures cannot be used to advantage. Any reference numerals in the claims should not be construed as limiting the scope of the present invention.

REFERENCE NUMERALS

100 Electrode carrier
101 Substrate
102 Conductive layer
103a, 103b Electrode lining
104 Insulating layer
105a, 105b Conductive adhesive
106 adhesive
107a, 107b Peel-off cover layer
109 Connection section
110a, 110b Inextendible section
111 Extendible section 112a, 112b Contact pad
113a, 113b, 113c Conductive track
201 Warpable member
202 String of warpable members
203 Cross bar
210 Inextendible section
211a-211e Extendible section
300 Electrode carrier
301 Replaceable electrode
302 Connection button

What is claimed is:

1. An electrode carrier for electrophysiological measurement, comprising:
a flexible substrate;
a plurality of contact pads attached to a substrate surface, wherein each contact pad comprises conductive means for accommodating an electrode for electrophysiological measurement;
first connecting means attached to the substrate for communicatively connecting the contact pads to a signal processing device;
wherein the first connecting means comprise a plurality of conductive tracks on the substrate surface for electrically connecting the plurality of contact pads, wherein each conductive track corresponds to at least one contact pad;
wherein the substrate has at least two inextendible sections for accommodating the contact pads;
wherein the at least two inextendible sections are interconnected by an extendible section;
wherein each extendible section comprises four warpable members of flexible material;
wherein at least one of the warpable members accommodates at least one of the conductive tracks;
wherein each warpable member has a first end connected to one of said inextendible sections, a second end, and a loop shaped portion extending between the first end and the second end; and
wherein the loop-shaped portions are arranged in an X-shape having a center formed by an interconnection member interconnecting the second ends of the four warpable members.

2. The electrode carrier according to claim 1, wherein the substrate is formed from a single sheet of flexible material.

3. The electrode carrier according to claim 1, wherein at least one of the inextendible sections of the substrate is provided with two contact pads and wherein at least one other inextendible section of the substrate is provided with a single contact pad.

4. The electrode carrier according to claim 1, wherein the contact pads are provided with second connecting means for attaching a removable electrode for electrophysiological measurement.

5. The electrode carrier according to claim 1, wherein at least one of the contact pads comprises one of more electrode linings for electrophysiological measurement.

6. The electrode carrier according to claim 5, wherein the at least one contact pad is provided with a dry electrode lining or a wet electrode lining.

7. The electrode carrier according to claim 5, wherein at least one contact pad comprises conductive gel or hydrogel lining.

8. The electrode carrier according to claim 7, wherein the conductive gel or hydrogel lining comprises an adhesive material.

9. The electrode carrier according to claim 8, wherein conductive gel or hydrogel is adhesive and/or has a high tack.

10. The electrode carrier according to claim 5, wherein the at least one contact pad has a surrounding adhesive layer with an opening to expose the electrode lining.

11. The electrode carrier according to claim 5, further comprising an adhesive conductive layer covering at least one electrode lining.

12. The electrode carrier according to claim 10, wherein the adhesive layer is covered by a removable cover layer.

13. The electrode carrier according to claim 1, wherein the conductive tracks comprise a conductive material selected from at least one of a metal, a conductive plastic material, and a metal containing ink.

14. The electrode carrier according to claim 1, wherein the conductive tracks are at least partially covered by an insulation layer.

15. The electrode carrier according to claim 1, wherein the electrode carrier is covered by an electromagnetic shielding layer.

16. The electrode carrier according to claim 15, wherein the electromagnetic shielding layer is connected to any one of the conductive tracks.

17. The electrode carrier according to claim 1, wherein the first connecting means comprise a connector having terminals, the terminal being electrically connected to the conductive tracks.

18. The electrode carrier according to claim 1, wherein the first connecting means comprise signal processing means connected to the conductive tracks, wherein the signal processing means comprises means for capturing and processing electrical signals from the contact pads.

19. The electrode carrier according to claim 18, wherein the signal processing means comprise an output connected to the connector.

20. The electrode carrier according to claim 18, wherein the first connecting means further comprise a wireless data transfer device, communicatively connected to the signal processing means, wherein the wireless data transfer device is arranged for wirelessly transferring the captured electrical signals and/or data derived from the captured electrical signals to the signal processing device.

* * * * *